(12) United States Patent
Gordley

(10) Patent No.: US 9,001,332 B1
(45) Date of Patent: Apr. 7, 2015

(54) COMPACT MULTI-CHANNEL GAS CORRELATION SENSOR AND SENSING METHODOLOGY

(71) Applicant: G&A Technical Software, Inc., Newport News, VA (US)

(72) Inventor: Larry L. Gordley, Grafton, VA (US)

(73) Assignee: G&A Technical Software, Inc., Newport News, VA (US)

( * ) Notice: Subject to any disclaimer, the term of this patent is extended or adjusted under 35 U.S.C. 154(b) by 0 days.

(21) Appl. No.: 14/068,016

(22) Filed: Oct. 31, 2013

(51) Int. Cl.
*G01N 21/00* (2006.01)
*G01N 21/3518* (2014.01)

(52) U.S. Cl.
CPC .................................. *G01N 21/3518* (2013.01)

(58) Field of Classification Search
CPC ........... G01B 2290/70; G01B 9/02007; G01B 11/2441; G01B 2290/45; G01B 9/0201; G01B 9/02027; G01B 9/02068; G01B 9/02077; G01B 9/0209; G01B 2290/35; G01B 9/0203; G01B 9/02; G01B 9/02039; G01B 9/02057
See application file for complete search history.

(56) References Cited

U.S. PATENT DOCUMENTS

| | | | |
|---|---|---|---|
| 6,210,464 B1 * | 4/2001 | Nakanishi et al. | ................ 95/52 |
| 2010/0163733 A1 * | 7/2010 | Prasad et al. | .................. 250/345 |

* cited by examiner

*Primary Examiner* — Michael P Stafira
(74) *Attorney, Agent, or Firm* — Peter J. Van Bergen

(57) ABSTRACT

A multi-channel gas correlation sensor and sensing method are provided. A spectral partitioning filter at the sensor's aperture or a pupil image thereof partitions a beam of light energy into unique spectral regions. Each spectral region is confined to a unique spatial region of the beam and passes light energy associated with a unique spectral band. The spectrally-partitioned beam undergoes a single split into two beams traversing a first path and a second path, respectively. Each of at least one gas of interest is disposed in only one of the first path and second path. Each gas at least partially absorbs/filters the light energy in at least one of the spectral regions. A detector is positioned such that each of the two beams form a pupil image on a unique portion of the detector after they traverse the first path and second path.

23 Claims, 4 Drawing Sheets

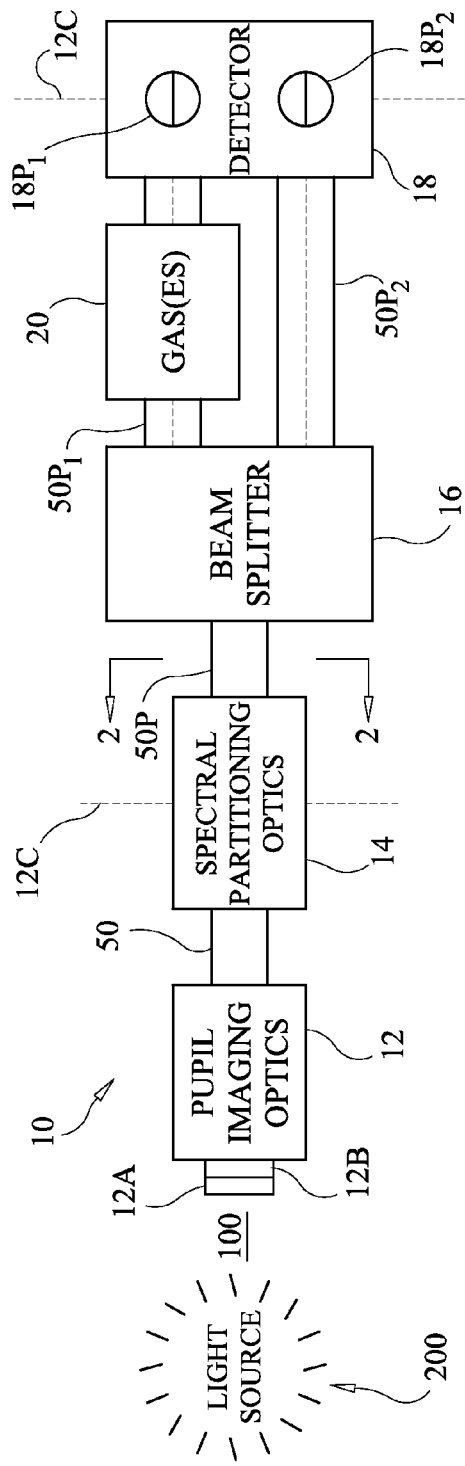
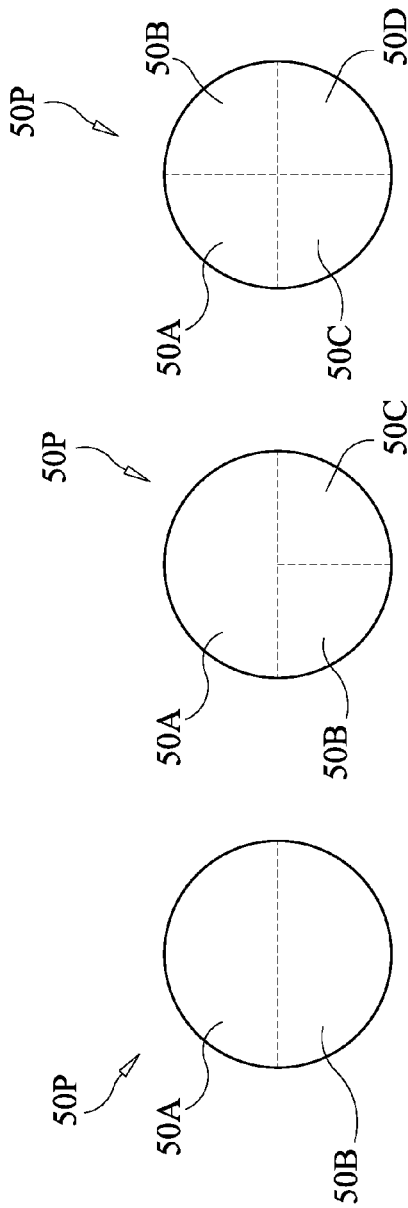
FIG. 1
FIG. 2A
FIG. 2B
FIG. 2C

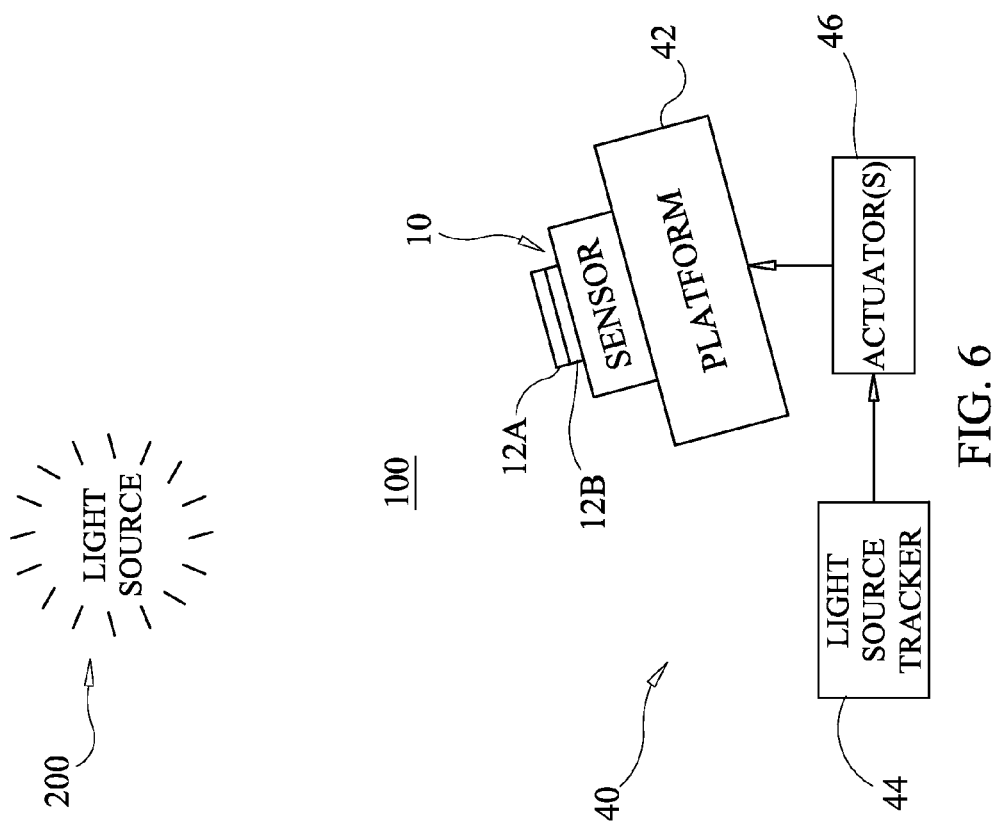

US 9,001,332 B1

COMPACT MULTI-CHANNEL GAS CORRELATION SENSOR AND SENSING METHODOLOGY

FIELD OF THE INVENTION

The invention relates generally to gas correlation, and more particularly to a multi-channel gas correlation sensor and sensing methodology that can process a beam of light energy to measure multiple gases simultaneously while only requiring a single split of the beam.

BACKGROUND OF THE INVENTION

Sensing the presence and/or concentration of a gas in a local environment or atmospheric region can employ a technology known generally as gas correlation. More specifically, gas filter correlation radiometry (GFCR) provides a method of creating a signal that is highly correlated (and highly filtered) to a specific gas, and therefore a good measure of that gas. However, for each gas measured, GFCR requires either a split beam pair or a gas-modulated beam filtered for that target gas. Thus, to apply GFCR to multiple gases, the instrument can become large, optically complex and expensive as the number of beam splitters increases.

SUMMARY OF THE INVENTION

Accordingly, it is an object of the present invention to provide a gas correlation sensor and sensing methodology that can simultaneously measure multiple gases.

Another object of the present invention is to provide a gas correlation sensor and sensing methodology that simplifies the measurement of multiple gases.

Other objects and advantages of the present invention will become more obvious hereinafter in the specification and drawings.

In accordance with the present invention, a sensor for performing multi-channel gas correlation sensing is provided. A pupil-imaging optical system forms a pupil image of a beam of light energy at a plurality of locations. A spectral partitioning filter is positioned at one of the pupil image locations so that the beam impinges thereon. The spectral partitioning filter partitions the beam into a plurality of unique spectral regions wherein each spectral region is confined to a unique spatial region of the beam and passes light energy associated with a unique spectral band. Beam splitting optics are positioned to receive the beam that has been partitioned into the spectral regions. The beam splitting optics generates two beams wherein one of the two beams traverses a first path and another of the two beams traverses a second path. Each beam has substantially identical spectral, polarization, and geometric qualities as the beam that impinged on the beam splitting optics. Each of at least one gas of interest is disposed in only one of the first path and second path. Each gas at least partially absorbs the light energy in at least one of the spectral regions. A detector is positioned at another of the pupil image locations to have each of the two beams form a pupil image on a unique portion of the detector after the one of the two beams traverses the first path and after the other of the two beams traverses the second path.

BRIEF DESCRIPTION OF THE DRAWINGS

Other objects, features and advantages of the present invention will become apparent upon reference to the following description of the preferred embodiments and to the drawings, wherein corresponding reference characters indicate corresponding parts throughout the several views of the drawings and wherein:

FIG. 1 is a schematic view of a multi-channel correlation sensor in accordance with an embodiment of the present invention;

FIG. 2A is a cross-sectional view of one embodiment of a spectrally partitioned beam taken along line 2-2 in FIG. 1;

FIG. 2B is a cross-sectional view of another embodiment of a spectrally partitioned beam;

FIG. 2C is a cross-sectional view of yet another embodiment of a spectrally partitioned beam;

FIG. 6 is a schematic view of a gas correlation sensor assembly that follows or tracks on a light source used in the measurement scenario in accordance with another embodiment of the present invention.

DETAILED DESCRIPTION OF THE INVENTION

Figure 3A:
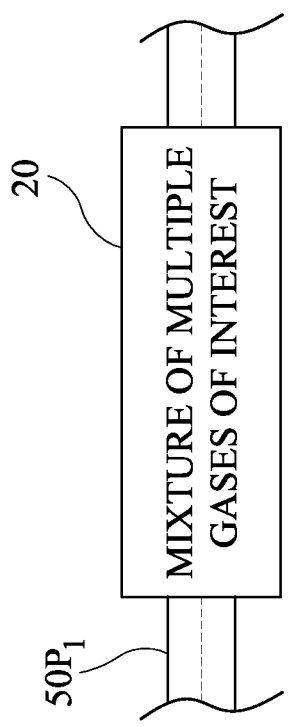
FIG. 3A is an isolated view of a single "gas of interest" region having multiple non-reactive gasses mixed therein.

Referring now to the drawings and more particularly to FIG. 1, a multi-channel gas correlation sensor in accordance with an embodiment of the present invention is shown and is referenced generally by numeral 10. Sensor 10 can be used to sense/measure the concentration of one gas or multiple gases in a region 100 between sensor 10 and a light source 200 that can be a natural light source (e.g., the sun, moon, etc.) or a man-made light source (e.g., an incandescent light, a glo-bar, etc.). Accordingly, region 100 can be an atmospheric region or a local gaseous environment without departing from the scope of the present invention.

Sensor 10 includes optics for forming a defocused far field scene that includes light source 200 such that the light energy associated therewith is uniformly distributed across the beam occurring at the sensor's aperture or pupil, or images of the aperture or pupil formed by the sensor's optics. As is known in the art, a totally defocused far field image can be achieved by imaging the aperture or pupil. For example, sensor 10 can include optics 12 for forming a pupil image using light energy emanating from light source 200 and passing through region 100. The pupil image is projected as a beam 50 of the light energy for imaging at a number of locations in sensor 10. To form the pupil image, an aperture 12A of optics 12 and field limiting optics 12B can be provided at the front end of optics 12. Aperture 12A allows light energy from light source 200 to enter sensor 10, and field limiting optics 12B is any optical scheme that images the field while limiting the field-of-view. Accordingly, as used herein, the phrase "pupil image location" can include aperture 12A as well as other pupil image locations within sensor 10. Since it is well known in the art how to create a field image in combination with a field stop placed at the field image, it is to be understood that the particular optical scheme used to achieve this is not a limitation of the present invention.

Beam 50 undergoes spectral partitioning at one of the pupil image locations. For example, spectral partitioning optics 14 can be placed in an optical plane located at the aperture 12A of optics 12 or optically after aperture 12A of optics 12 at one of the pupil image locations 12C defined in sensor 10. Examples of spectral partitioning optics 14 include, but are not limited to, butcher block filters and monolithic array filters. Regardless of the type of spectral partitioning filter optics used, optics 14 is positioned at an aperture stop (i.e., a pupil image location) of optics 12. Spectral partitioning filters are available from a variety of commercial sources.

In general, spectral partitioning optics 14 spectrally partitions beam 50 into two or more spectral regions. As used herein, the term "spectral region" refers to a unique spatial region of beam 50 with each such spatial region passing light energy (in beam 50) associated with a unique spectral band. For example, FIG. 2A depicts a cross-section of a spectrally-partitioned beam 50P (i.e., beam 50 after spectral partitioning) into two-equally-sized spectral regions 50A and 50B. However, the present invention is not so limited as FIG. 2B depicts a cross-section of beam 50P partitioned into three spectral regions 50A, 50B and 50C that are not equal in size. FIG. 2C depicts a cross-section of beam 50P partitioned into four equally-sized spectral regions 50A-50D. Accordingly, it is to be understood that the number, size, and/or shape of the spectral partitions of beam 50P are not limitations of the present invention.

Spectrally partitioned beam 50P is passed to a beam splitter 16 that performs a single optical beam split on beam 50P. More specifically, beam splitter 16 generates two beams $50P_1$ and $50P_2$ in such a way that each one maintains (or substantially maintains within the limits of available optics) the spectral, polarization, and geometric qualities associated with the spectrally-partitioned beam 50 impinging on beam splitting optics 16. The particular configuration/construction of beam splitter 16 to generate two such beams $50P_1$ and $50P_2$ is not a limitation of the present invention. Each of beams $50P_1$ and $50P_2$ traverses a unique path (e.g., non-overlapping paths) prior to each beam impinging on a unique region of a detector 18 located at another pupil image location 12C of optics 12 thereby forming independent images of the spectrally-partitioned beams. Detector 18 can be a conventional two-dimensional array of detector elements that can be used to independently sense each partition. It is to be understood that detector 18 includes commercially-available two-dimensional array detectors, or custom-constructed detectors using individual detector elements arranged to allow independent sensing of spectral regions. Accordingly, it is to be understood that the detector design for sensing the spectrally-partitioned regions is not a limitation of the present invention.

Prior to impinging on detector 18, beam $50P_1$ is passed through a region 20 having one or more gases of interest residing therein. As will be explained further below by way of several examples, one of the great advantages of the present invention is its ability to be readily adapted to provide a multi-channel GFCR response for just one gas of interest or a multi-channel GFCR response for multiple gases of interest using only a single-split of spectrally-partitioned beam 50P. In the FIG. 1 embodiment, gas region 20 is only disposed in beam $50P_1$. However, and as will be explained later below, other gas(es) of interest could be disposed in beam $50P_2$.

As used in herein, the term "gas of interest" refers to a gas that may be in region 100 and that sensor 10 is capable of detecting/measuring. Each such gas should be at least partially absorbed by one (or more) of the spectral regions of beams $50P_1/50P_2$. However, each such gas can only be disposed in one of beams $50P_1$ and $50P_2$.

In the FIG. 1 embodiment, region 20 could contain a single gas of interest that will at least partially absorb the light energy in each spectral region of beam 50P. This embodiment is useful in measurement strategies to improve the accuracy and calibration of sensor 10. For example, if there are additional gases in region 100 that are not of interest but still would produce a residual gas correlation signal, the signals from the different spectral regions can yield information about the additional gases.

Since beam $50P_2$ will not contain the gas of interest, the two uniquely imaged/detected pupil images $18P_1$ and $18P_2$ at detector 18 yield gas correlation measurements. That is, image $18P_1$ is a pupil image that presents gas filtered data, while image $18P_2$ is a pupil image that presents a gas "void" data, i.e., no gas filtering or absorption of the gas of interest occur in beam $50P_2$. Typically, images $18P_1$ and $18P_2$ will be formed at unique and non-overlapping portions of detector 18. However, the present invention could also be practiced using two partially overlapped pupil images at detector 18 provided the subsequent measurement processing only "looked" at the non-overlapped or unique portions of the images. Processing of the measurements (generated by images $18P_1$ and $18P_2$) at detector 18 to yield a gas concentration as in region 100 are well understood in the art and do not limit the scope of the present invention.

Figure 3B:
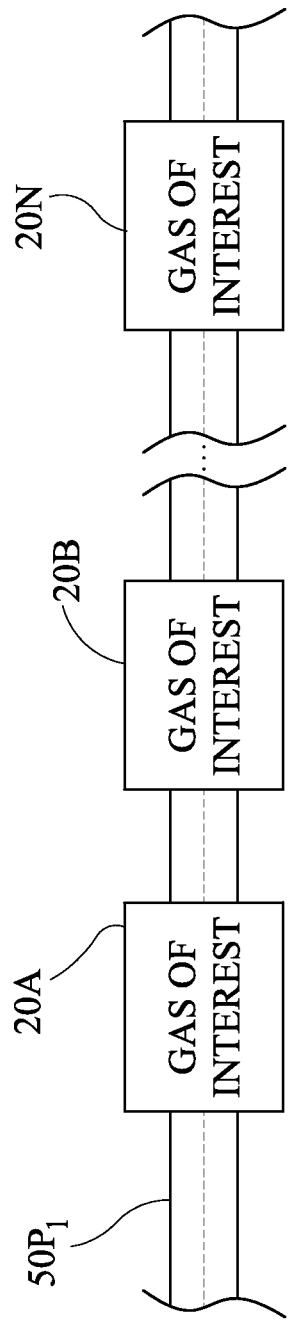
FIG. 3B is an isolated view of separate and sequentially-arranged gas regions with each one having a single "gas of interest"

As mentioned above, multiple gases of interest could be provided in region 20. If the gases do not react with one another, multiple non-reactive gases can be mixed in region 20 as shown in FIG. 3A. However, if the gases did react with one another or if the gases required different conditions for proper containment (e.g., maintenance of particular temperature and/or pressure conditions), the multiple gases (e.g., N gases) could be provided in separate regions 20A, . . . , 20N arranged sequentially along beam $50P_1$ as shown in FIG. 3B. This is possible as long as the gas of interest in any one of regions 20A, . . . , 20N will not absorb the light energy intended to be absorbed in another of regions 20A, . . . , 20N. It is to be further understood that a combination of mixed gas regions and single-gas regions could be employed without departing from the scope of the present invention.

Figure 4:
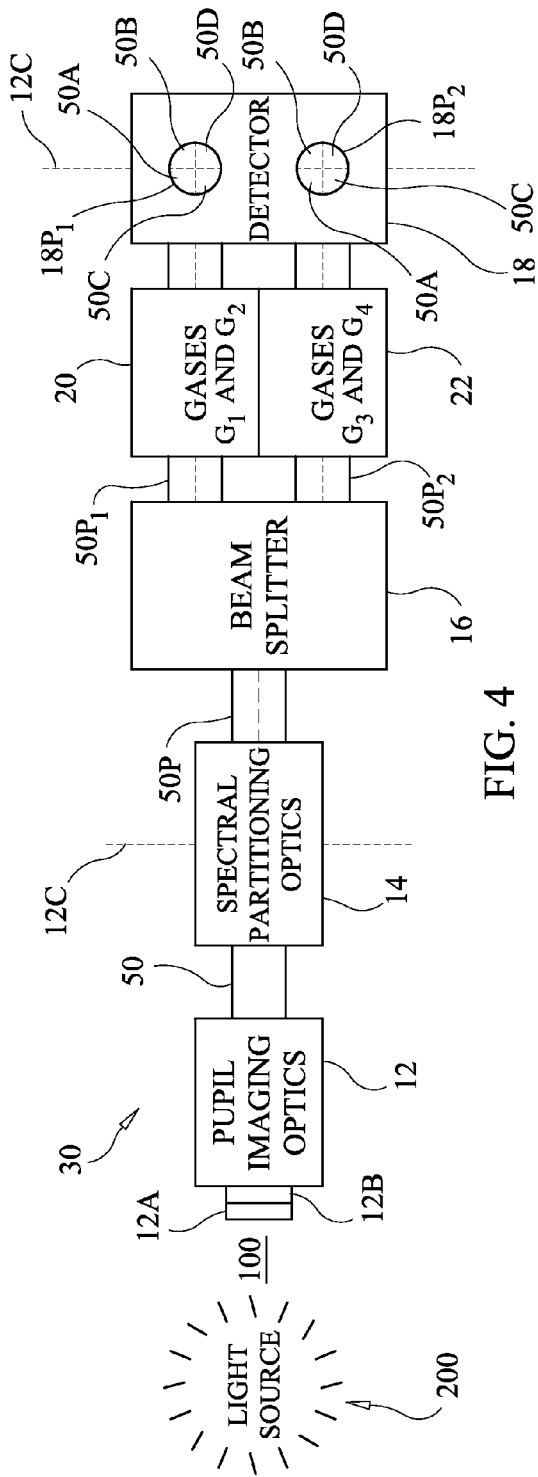
FIG. 4 is a schematic view of a multi-channel gas correlation sensor in accordance with another embodiment of the present invention.

As also mentioned above, the sensor of the present invention can be readily configured with multiple channels to sense/measure multiple gases with various gases of interest disposed in both beams $50P_1$ and $50P_2$. For example, FIG. 4 illustrates another gas correlation sensor 30 having a "gas of interest" region 20 disposed in beam $50P_1$ and a "gas of interest" region 22 disposed in beam $50P_2$. As with the earlier-described embodiments, each region 20/22 can define a single region of mixed gases, a sequential arrangement of single-gas regions, or a combination thereof, without departing from the scope of the present invention. By way of an illustrative example, it will be assumed that region 20 includes gases $G_1$ and $G_2$ while region 22 includes gases $G_3$ and $G_4$. It is further assumed that beam 50 is spectrally partitioned into four spectral regions (e.g., as shown in FIG. 2C) with each region at least partially absorbing light energy associated with a unique one of gases $G_1$-$G_4$. For example, assume the spectral band of spectral region 50A is absorbed by gas $G_1$, the spectral band of spectral region 50B is absorbed by gas $G_2$, the spectral band of spectral region 50C is absorbed by gas $G_3$, and the spectral band of spectral region 50D is absorbed by gas $G_4$. In this way, image $18P_1$ provides absorption data for gases $G_1$ and $G_2$ while image $18P_2$ provides "void" data for gases $G_1$ and $G_2$. Conversely, image $18P_2$ provides absorption data for gases $G_3$ and $G_4$ while image $18P_1$ provides "void" data for gases $G_3$ and $G_4$.

Figure 5:
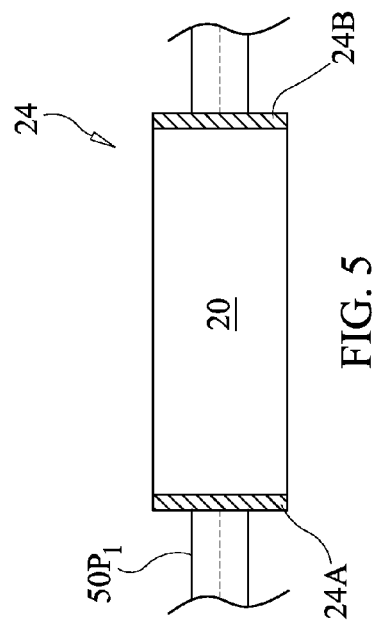
FIG. 5 is an isolated cross-sectional view of a gas cell used to define a "gas of interest" region in accordance with an embodiment of the present invention.

Regions 20 and 22 can be defined in a variety of ways without departing from the scope of the present invention. For example, a sensor 10 (or 30) of the present invention could be constructed as a sealed assembly in which case regions 20/22 could be defined therein. However, each of regions 20 and 22 could be defined by a gas cell as shown in FIG. 5. For example, a gas cell 24 defining region 20 therein can have optically-transmitting ends 24A and 24B that allow beam 50P$_1$ to pass through. The one or more gases of interest can be contained between optically-transmitting ends 24A and 24B.

The advantages of the present invention are numerous. The spectrally-partitioned pupil-image beam need only be subject to a single beam splitting operation to develop a multi-channel gas correlation sensor. This will greatly reduce the size, cost, and complexity for multi-channel gas correlation sensors. As described herein, multiple channels can be used in the context of sensing/measuring a single "gas of interest" or multiple gases of interest.

The simplicity of the present invention's single split beam will provide for a compact gas correlation sensor assembly. By virtue of this feature, the present invention can be readily adapted for use in atmospheric or gaseous-region monitoring sensors that are placed at fixed locations or on mobile platforms. All that is required is for the sensor to be aligned with a light source as either the light source moves and/or the sensor's mounting platform moves. Accordingly, FIG. 6 illustrates a gas correlation sensor assembly 40 having a movable platform 42 for support of (for example) sensor 10 as described above. Typically, aperture 12A (and sensor 10) will be fixed in relation to one another for coordinated movement with platform 42. A light source tracker 44 can be provided adjacent to (or on) platform 42. Tracker 44 is any element or combination of elements that can locate light source 200 and determine its location relative to aperture 12A. For example, if light source 200 is the sun or moon, tracker 44 could include GPS location electronics to determine the location of sensor assembly 40 that, when combined with a time of day, can readily determine the bearing of light source 200 relative to sensor assembly 40. The bearing of light source 200 can be provided to an actuator(s) 46 (e.g., motors, solenoid drives, etc.) for the repositioning of platform 42 so that aperture 12A will align with light source 200. It is to be understood that the details of such a sensor assembly 40 can be implemented in a variety of ways without departing from the scope of the present invention.

Although the invention has been described relative to a specific embodiment thereof, there are numerous variations and modifications that will be readily apparent to those skilled in the art in light of the above teachings. It is therefore to be understood that, within the scope of the appended claims, the invention may be practiced other than as specifically described.

What is claimed as new and desired to be secured by Letters Patent of the United States is:

1. A multi-channel gas correlation sensor, comprising:
a pupil-imaging optical system for forming a pupil image of a beam of light energy at a plurality of locations;
a spectral partitioning filter positioned at one of said locations wherein said beam impinges thereon, said spectral partitioning filter partitioning said beam into a plurality of unique spectral regions wherein each of said spectral regions is confined to a unique spatial region of said beam and passes light energy associated with a unique spectral band;
beam splitting optics positioned to receive said beam partitioned into said spectral regions, said beam splitting optics generating two beams wherein one of said two beams traverses a first path and another of said two beams traverses a second path, each of said two beams having substantially identical spectral, polarization, and geometric qualities as said beam impinging on said beam splitting optics;
at least one gas of interest, each said gas being disposed in only one of said first path and said second path, each said gas at least partially absorbing said light energy in at least one of said spectral regions; and
a detector positioned at another of said locations to have each of said two beams impinge on a unique portion of said detector after said one of said two beams traverses said first path and after said another of said two beams traverses said second path.

2. A multi-channel gas correlation sensor as in claim 1, wherein said spectral partitioning filter is located at an aperture of said pupil-imaging optical system.

3. A multi-channel gas correlation sensor as in claim 1, wherein said spectral partitioning filter is located optically after an aperture of said pupil-imaging optical system.

4. A multi-channel gas correlation sensor as in claim 1, wherein said spectral partitioning filter is selected from the group consisting of butcher block filters and monolithic array filters.

5. A multi-channel gas correlation sensor as in claim 1, wherein said pupil-imaging optical system includes an aperture for admitting said beam, said sensor further comprising:
a platform for support of said pupil-image optical system, wherein said aperture and said platform are in fixed relation to one another;
a tracker adapted to track a location of a source of said light energy; and
an actuator coupled to said tracker and said platform for moving said platform based on the location of the source to align said aperture with said light energy from the source.

6. A multi-channel gas correlation sensor as in claim 1, wherein said at least one gas comprises a plurality of gases disposed in said first path.

7. A multi-channel gas correlation sensor as in claim 6, wherein said plurality of gases are mixed together.

8. A multi-channel gas correlation sensor as in claim 6, wherein said plurality of gases are separated from one another and are arranged sequentially along said first path.

9. A multi-channel gas correlation sensor as in claim 1, wherein said at least one gas comprises:
a first plurality of gases disposed in said first path; and
a second plurality of gases disposed in said second path.

10. A multi-channel gas correlation sensor, comprising:
a pupil-imaging optical system for forming a pupil image of a beam of light energy at a plurality of locations;
a spectral partitioning filter positioned at one of said locations wherein said beam impinges thereon, said spectral partitioning filter partitioning said beam into a plurality of unique spectral regions wherein each of said spectral regions is confined to a unique spatial region of said beam and passes light energy associated with a unique spectral band;
beam splitting optics positioned to receive said beam partitioned into said spectral regions, said beam splitting optics generating two beams wherein one of said two beams traverses a first path and another of said two beams traverses a second path, each of said two beams having substantially identical spectral, polarization, and geometric qualities as said beam impinging on said beam splitting optics;
at least one optically-transmitting gas cell disposed in said first path;

at least one optically-transmitting gas cell disposed in said second path;

at least one gas populating at least one said optically-transmitting gas cell, each said gas being disposed in only one of said first path and said second path, each said gas at least partially absorbing said light energy in at least one of said spectral regions; and a detector positioned at another of said locations to have each of said two beams impinge on a unique and non-overlapped portion of said detector after said one of said two beams traverses said first path and after said another of said two beams traverses said second path.

11. A multi-channel gas correlation sensor as in claim 10, wherein said spectral partitioning filter is located at an aperture of said pupil-imaging optical system.

12. A multi-channel gas correlation sensor as in claim 10, wherein said spectral partitioning filter is located optically after an aperture of said pupil-imaging optical system.

13. A multi-channel gas correlation sensor as in claim 10, wherein said spectral partitioning filter is selected from the group consisting of butcher block filters and monolithic array filters.

14. A multi-channel gas correlation sensor as in claim 1, wherein said pupil-imaging optical system includes an aperture for admitting said beam, said sensor further comprising:
a platform for support of said pupil-image optical system, wherein said aperture and said platform are in fixed relation to one another;
a tracker adapted to track a location of a source of said light energy; and
an actuator coupled to said tracker and said platform for moving said platform based on the location of the source to align said aperture with said light energy from the source.

15. A multi-channel gas correlation sensor as in claim 10, wherein said at least one gas comprises a plurality of gases disposed in said first path.

16. A multi-channel gas correlation sensor as in claim 15, wherein said plurality of gases are mixed together in one said optically-transmitting gas cell.

17. A multi-channel gas correlation sensor as in claim 15, wherein said at least one optically-transmitting gas cell in said first path comprises a sequential series of optically-transmitting gas cells along said first path, and wherein each of said plurality of gases populates one of said optically-transmitting gas cells in said sequential series.

18. A multi-channel gas correlation sensor as in claim 10, wherein said at least one optically-transmitting gas cell disposed in said first path comprises a first cell and wherein a first plurality of gases are disposed in said first cell; and
wherein said at least one optically-transmitting gas cell disposed in said second path comprises a second cell and wherein a second plurality of gases are disposed in said second cell.

19. A method of performing multi-channel gas correlation sensing, comprising the steps of:
forming a pupil image of a beam of light energy at a plurality of locations;
spectrally partitioning said beam at one of said locations into a plurality of unique spectral regions, wherein each of said spectral regions is confined to a unique spatial region of said beam and passes light energy associated with a unique spectral band;
splitting said beam partitioned into said spectral regions to generate two beams, wherein one of said two beams traverses a first path and another of said two beams traverses a second path, each of said two beams having substantially identical spectral, polarization, and geometric qualities as said beam prior to said step of splitting;
providing at least one gas of interest, each said gas being disposed in only one of said first path and said second path, each said gas at least partially absorbing said light energy in at least one of said spectral regions; and
detecting each of said two beams uniquely at another of said locations after said one of said two beams traverses said first path and after said another of said two beams traverses said second path.

20. A method according to claim 19, wherein said at least one gas comprises a plurality of gases disposed in said first path.

21. A method according to claim 20, wherein said plurality of gases are mixed together.

22. A method according to claim 20, wherein said plurality of gases are separated from one another and are arranged sequentially along said first path.

23. A method according to claim 19, wherein said at least one gas comprises:
a first plurality of gases disposed in said first path; and
a second plurality of gases disposed in said second path.

* * * * *